(12) United States Patent
Shoji

(10) Patent No.: US 7,378,490 B1
(45) Date of Patent: May 27, 2008

(54) CYCLIC PEPTIDES AND AIDS VACCINES

(75) Inventor: Shozo Shoji, Kumamoto (JP)

(73) Assignee: Nissui Pharmaceutical Co., Ltd. (JP)

( * ) Notice: Subject to any disclaimer, the term of this patent is extended or adjusted under 35 U.S.C. 154(b) by 0 days.

(21) Appl. No.: 09/889,845

(22) PCT Filed: Nov. 5, 1999

(86) PCT No.: PCT/JP99/06174

§ 371 (c)(1),
(2), (4) Date: Jul. 23, 2001

(87) PCT Pub. No.: WO00/47609

PCT Pub. Date: Aug. 17, 2000

(30) Foreign Application Priority Data

Feb. 10, 1999 (JP) .................... 11-032990

(51) Int. Cl.
*A61K 38/12* (2006.01)

(52) U.S. Cl. .............. 530/317; 530/327; 424/188.1

(58) Field of Classification Search ............. 424/184.1; 530/300, 327, 317
See application file for complete search history.

(56) References Cited

FOREIGN PATENT DOCUMENTS

| EP | 0 551 689 A2 | 1/1992 |
| EP | 0 834 564 A2 | 4/1998 |
| JP | 08-027184 | 1/1996 |
| WO | WO 97/47319 | 12/1997 |

OTHER PUBLICATIONS

Feinberg, M. B., and J. P. Moore, 2002, "AIDS vaccine models: challenging challenge viruses.", Nature Med. 8(3):207-210.*
Bende, S., and M. I. Johnston, 2000, "Update: search for an AIDS vaccine.", AIDS Reader 526-538.*
Johnston, M. I., 2000, "The role of nonhuman primate models in AIDS vaccine development.", Mol. Med. Today 6:267-270.*
Moore, J. P., and D. R. Burton, 1999, "HIV-1 neutralizing antibodies: how full is the bottle?", Nature Med. 5(2):142-144.*
Burton, D. R., and J. P. Moore, 1998, "Why do we not have an HIV vaccine and how can wemake one?", Nature Med. Vaccine Suppl. 4(5):495-498.*
Letvin, N. L., 1998, "Progress in the development of an HIV-1 vaccine.", Science 280:1875-1880.*
Lee, T.-H., 1997, "Acquired immunodeficiency disease vaccines: design and development", in *AIDS: Biology, Diagnosis, Treatment and Prevention, fourth edition*, DeVita, Jr., V. T., et al., eds., Lippincott-Raven Publishers, Philadelphia, PA, pp. 605-616.*
Haynes, B. F., et al., 1996, "Update on the issues of HIV vaccine development.", Annals Med. 28:39-41.*
Feng, Y., Broder, C., Kennedy, P., Berger, E. Science., vol. 272. pp. 872-877. May 10, 1996.
Liu, R. et al. Cell, vol. 86. pp. 367-377. Aug. 9, 1996.
Olson, W. et al. Journal of Virology, vol. 73, No. 5. pp. 4145-4155. May 1999.
Brelot, A., Heveker, N., Pleskoff, O., Sol., N., Alizon, M. Journal of Virology, vol. 71, No. 6. pp. 4744-4751. Jun. 1997.
Biochemical and Biophysical Research Communications 285, 1309-1316 (2001).
The Journal of Biological Chemistry, vol. 278, No. 34, Issue of Aug. 22, pp. 32335-32343, 2003.
Stat Med. Jul. 30, 2003; 22(14):2281-98, On the analysis of viral load endpoints in HIV vaccine trials.
Japan Pharmacology Academy Kyushu Branch Mass Meeting Lecture Summary Collection, pp. 43.

* cited by examiner

*Primary Examiner*—Jeffrey S. Parkin
(74) *Attorney, Agent, or Firm*—Bacon & Thomas, PLLC

(57) ABSTRACT

Cyclic peptides comprising, as a constituent chain or chains, one or two amino acid sequences selected from the groups consisting of the amino acid sequence Glu-Ala-Asp-Asp-Arg and the amino acid sequence Ser-Gln-Lys-Glu-Gly, and AIDS vaccines containing the cyclic peptide as an active ingredient. Preferably a cyclic dodecapeptide represented by the formula given below and an AIDS vaccine containing the cyclic dodecapeptide as an active ingredient. From the in vivo absorption and antibody formation viewpoint, active groups selected from among the carboxyl, amino and hydroxyl groups contained in the cyclic peptide is preferably bound to substituent groups. The cyclic dodecapeptide can neutralize the second receptors in the infection of human with HIV-1 virus

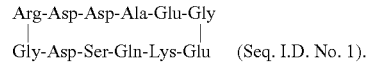

3 Claims, 2 Drawing Sheets

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      cyclo-oligo peptide

<400> SEQUENCE: 1

Arg Asp Asp Ala Glu Gly Glu Lys Gln Ser Asp Gly
  1               5                  10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ala Asp Asp Arg
  1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
-continued

<400> SEQUENCE: 3

Ser Gln Lys Glu Gly
 1               5
```

US 7,378,490 B1

CYCLIC PEPTIDES AND AIDS VACCINES

CROSS-REFERENCE TO RELATED APPLICATIONS

Figure 1:
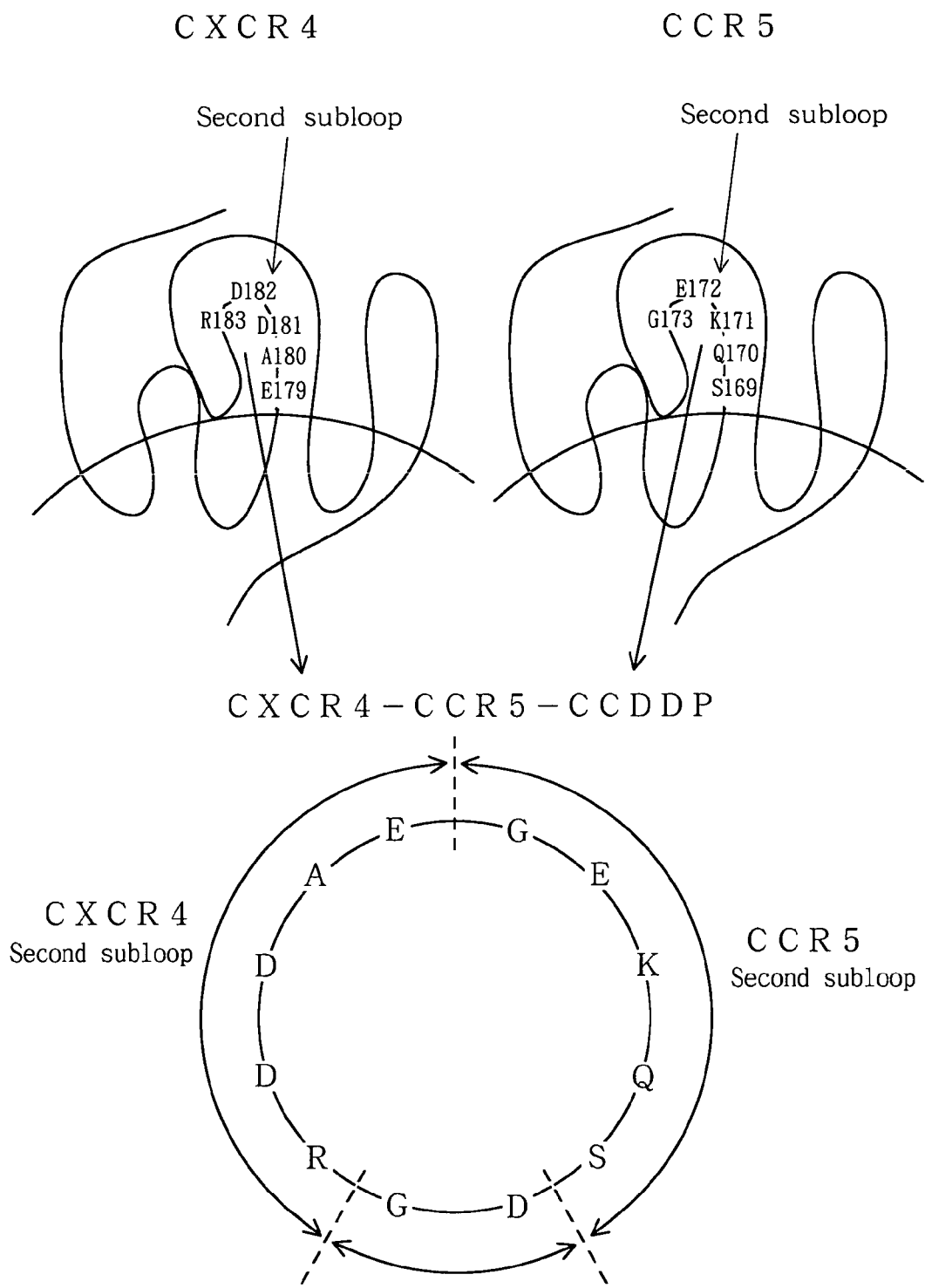

This application is a National Phase Application (35 USC 371) of PCT/JP99/06174, filed Nov. 5, 1999 and claims priority of Japanese Application No. 11-32990, filed Feb. 10, 1999.

FIELD OF THE INVENTION

The present invention relates to cyclic peptides effective in preventing HIV-1 virus infection in human and to AIDS vaccines. More particularly, it relates to cyclic peptides which serve as antigens for producing a neutralizing antibody capable of neutralizing HIV-1 virus infection via the second receptors called CXCR4 and CCR5 and to AIDS vaccines which comprise the above antigens as active ingredients.

BACKGROUND OF THE INVENTION

Second receptors which the pathogenic virus causative of AIDS (HIV-1 virus) utilizes in infecting human were identified in 1996 (Yu Feng et al., Science, 272, 872-877, 1996). These two receptors are called CXCR4 and CCR5. It has been revealed that the HIV-1 virus utilizes one of the receptors for adsorption onto and entry into lymphocytes, macrophages and dendritic cells to achieve infection.

On the other hand, about 1 to 2% of Caucasians reportedly have resistance to HIV-1 virus infection and it has been revealed that this is due to a genetic defect or genetic incompleteness of the second receptors (CXCR4 and CCR5), which are chemokine receptors (Rong Liu et al., 86, 367-377, 1996).

These findings have called researchers attention to the importance of neutralization of the second receptors in the prevention of HIV-1 virus infection and, in recent years, attempts have been made to produce a neutralizing antibody capable of neutralizing the second receptors. There is no report, however, of the successful creation of such a neutralizing antibody.

Accordingly, it is an object of the present invention to provide three-dimensional antigens capable of producing, in vivo, a neutralizing antibody capable of neutralizing the second receptors from the stereoscopic viewpoint by paying attention to the loop structures of the second receptor proteins without following the conventional methods which interpret the peptides constituting the second receptors two-dimensionally. Another object is to provide AIDS vaccines which comprise such antigens as active ingredients.

DISCLOSURE OF THE INVENTION

The present inventors constructed a model of the second receptor in T cells (abbr.: CXCR4) and a model of the second receptor in macrophages (abbr.: CCR5) and observed them from a three-dimensional viewpoint. As a result, they explored the applicability of two pentapeptides constituting the second subloop (UPL) in the respective second receptor proteins, namely T cell-derived $Glu_{179}$-$Ala_{180}$-$Asp_{181}$-$Asp_{182}$-$Arg_{183}$ (Seq. I.D. No. 2) and macrophage-derived $Ser_{169}$-$Gln_{170}$-$Lys_{171}$-$Glu_{172}$-$Gly_{173}$ (Seq. I.D. No. 3), as constituent elements of a novel antigen for producing an HIV-1 virus infection-preventing antibody capable of neutralizing the second receptors.

Thus, the present invention provides a cyclic peptide which is a novel compound and which comprises, as a constituent chain thereof, one or two amino acid sequences selected from among amino acid sequences contained in the second subloop in the T cell second receptor protein and comprising at least five amino acid residues and amino acid sequences contained in the second subloop in the macrophage second receptor protein and comprising at least five amino acid residues. The present invention further provides AIDS vaccines comprising that compound as an active ingredient.

More specifically, the cyclic peptide of the present invention, which is a novel compound, is characterized in that it comprises one or two amino acid sequences selected from the groups consisting of the amino acid sequence Glu-Ala-Asp-Asp-Arg (Seq. I.D. No. 2) and the amino acid sequence Ser-Gln-Lys-Glu-Gly (Seq. I.D. No. 3) as a constituent chain or chains thereof, and the AIDS vaccine is characterized by comprising such compounds as active ingredients.

More particularly, the cyclic peptide of the invention is characterized in that it is a novel compound which is represented by the formula (1) given below and the AIDS vaccine of the invention is characterized in that it comprises that compound as an active ingredient.

$$\begin{array}{c} \text{Arg-Asp-Asp-Ala-Glu-Gly} \\ | \qquad\qquad\qquad\qquad | \\ \text{Gly-Asp-Ser-Gln-Lys-Glu} \end{array} \quad \text{(Seq. I.D. No. 1)} \qquad \text{Formula (1)}$$

FIG. 1 shows the configuration of a T cell-derived second receptor protein molecule on the T cell membrane (FIG. 1, top left) and the configuration of a macrophage-derived second receptor protein molecule on the macrophage membrane (FIG. 1, top right) and a cyclic dodecapeptide according to the invention as synthesized from the respective second subloop peptides of these second receptor protein molecules. In FIG. 1, the T cell-derived second receptor protein molecule (CXCR4) has a configuration comprising a first loop, a second loop, a third loop and a second subloop and the macropahge-derived second receptor protein molecule (CCR5) also has a configuration comprising a first loop, a second loop, a third loop and a second subloop.

The second subloop in the T cell-derived second receptor protein molecule (CXCR4) contains the amino acid sequence $Glu_{179}$-$Ala_{180}$-$Asp_{181}$-$Asp_{182}$-$Arg_{183}$ (Seq. I.D. No. 2) and the second subloop in the macrophage-derived second receptor protein molecule (CCR5) contains the amino acid sequence $Ser_{169}$-$Gln_{170}$-$Lys_{171}$-$Glu_{172}$-$Gly_{173}$ (Seq. I.D. No. 3).

A novel compound cyclic dodecapeptide of the present invention as represented by the formula (1) shown above (cyclic peptide shown in FIG. 1, bottom) can be obtained by causing both the peptides respectively having the above-identified amino acid sequences of both the second subloops of CXCR4 and CCR5 to form a ring via -Gly-Asp- as a spacer arm dipeptide.

Preferably, an active group selected from among the carboxyl, amino and hydroxyl groups contained in the cyclic dodecapeptide represented by the above formula (1) is bonded to a substituent group so that the absorption into the living body and antibody formation may be facilitated. Such a substituent can be selected from among the residues of fatty acids $CH_3(CH_2)_n$—COOH (n: 0 to 20), the residues of alcohols $CH_3(CH_2)_n$—OH (n: 0 to 20) and the unsaturated compound residues corresponding to such compound residues and preferably has biocompatibility. As appropriate examples of the fatty acid, there may be mentioned lauric acid, myristic acid, palmitic acid, stearic acid, arachidonic acid, and unsaturated fatty acids corresponding thereto. As appropriate higher alcohols, there may be mentioned lauryl alcohol, myristyl alcohol, palmityl alcohol, stearyl alcohol, eicosanol, and unsaturated alcohols corresponding thereto.

The cyclic dodecapeptide represented by the above formula (1) can be utilized as an immunogen for producing a second receptor neutralizing antibody capable of inhibiting HIV-1 virus infection.

An assaying antigen for antibody screening is prepared by binding the cyclic dodecapeptide to a solid phase resin. Separately, mice were immunized with an immunogen, for example a cyclic dodecapeptide-multiple antigen peptide (abbr.: CDP-MAP), and monoclonal antibodies are prepared by the conventional hybridoma technique. For confirming the anti-infective activity against HIV-1 virus infection, several hybridomas (cells produced by fusion of antibody-producing B cells and myeloma cells (cancer cells)) are prepared by the above method and anti-HIV-1 virus activity assaying is carried out in the conventional manner using the hybridoma culture supernatants, to show the culture supernatants prevent HIV-1 virus infection.

Thus, the cyclic dodecapeptide represented by the formula (1) can be used as an immunogen for producing antibodies having inhibitory effects against HIV-1 virus infection and therefore is useful as an active agent in AIDS vaccines.

The AIDS vaccines according to the invention contain as an active agent, a cyclic peptide comprising, as a constituent chain or chains thereof, one or two amino acid sequences selected from the amino acid sequence Glu-Ala-Asp-Asp-Arg (Seq. I.D. No. 2) and the amino acid sequence Ser-Gln-Lys-Glu-Gly (Seq. I.D. No. 3).

The AIDS vaccines according to the invention may comprise the above cyclic peptides as active agents or the active agents may be modifications of the cyclic peptides by substitution and/or addition or may be in the form of a pharmacologically acceptable salt. Pharmacologically acceptable salts include salts with hydrochloric acid, sulfuric acid, nitric acid, nitrous acid, hydrobromic acid, hydroiodic acid, phosphoric acid and organic acids.

An example of a suitable derivative (modification) of the compound of the above formula (1) is that in which the substituent group is a higher fatty acid group as shown below.

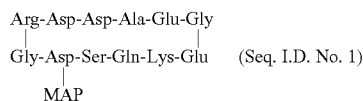

Formula (2)  (Seq. I.D. No. 1)

Five equivalents of 9-fluorenylmethoxycarbonyl-dimethylsulfonium methyl sulfate (Fmoc-DSP; tradename, product of Novabiochem) are added to 1 equivalent of the cyclic dodecapeptide-MAP represented by the formula (2) to thereby block the ε-amino group of $K_4$ of the cyclic dodecapeptide-MAP and then the carboxyl groups ($E_5$, $E_7$, $D_9$, $D_{10}$) are activated with EDC, DCC, BOP or the like, and a higher alcohol [$CH_3(CH_2)_n$—OH] is added in excess to thereby effect esterification. Alternatively, the hydroxyl group of Ser of the cyclic dodecapeptide-MAP represented by the above formula (2) is esterified by the acid chloride [$CH_3(CH_2)_n COCl$] method and, after elimination of Fmoc, the ester is used as a base material of the peptide vaccine. When the vaccine is administered to a living body, it is delivered to lymphoid tissues where the ester is hydrolyzed. The thus-recovered original cyclic peptide-MAP represented by formula (2) activates the immune system, whereby antibodies are produced and the AIDS virus infection is neutralized.

The AIDS vaccines according to the invention can be used as pharmaceutical compositions in the form or oral or nonoral preparations. The oral dosage form includes tablets, powders, granules, capsules, microcapsules, solutions and the like. The nonoral or parenteral dosage form includes solutions, mainly injectable solutions, and suppositories, among others. Generally, these preparations may contain one or more pharmaceutical preparation auxiliaries such as carriers, excipients, binders, disintegrants, lubricants, stabilizers, flavors, and the like.

The dose may vary according to the symptom and/or age. In the case of oral administration, a daily dose of 0.1 to 1000 mg/kg body weight can be administered to normal adults.

BEST MODES FOR CARRYING OUT THE INVENTION

Example 1

(1) Synthesis of a Cyclic Chimera Peptide Comprising Second Subloop Peptides of Two Types of Receptors for HIV-2

The resin used for solid synthesis of the peptide was a 2-chlorotrisyl chloride resin, which will not impair the protective groups on various amino acid residues and from which the peptide can be cleaved with a weak acid. A 0.25-mmol (368-mg) portion of the resin was weighed and used. The peptide synthesis was carried out according to the Fmoc (9-fluorenylmethoxycarbonyl) chemistry and a Fmoc-side chain-protected peptide-resin was obtained by starting the synthesis from the C terminus on a fully automated peptide synthesizer using the following Fmoc-side chain-protected amino acids 1) to 12) (1.0 mmol each).

1) Fmoc-Gly-OH 1.0 mmol

2) Fmoc-L-Arg(Pmc)-OH 1.0 mmol
   Pmc: 2,2,5,7,8-pentamethylchroman-6-sulfonyl

3) Fmoc-L-Asp(OtBu)-OH 1.0 mmol
   OtBu: O-t-butyl

4) Fmoc-L-Asp(OtBu)-OH 1.0 mmol

5) Fmoc-L-Ala-OH 1.0 mmol

6) Fmoc-L-Glu(OtBu)-OH 1.0 mmol

7) Fmoc-Gly-OH 1.0 mmol

8) Fmoc-L-Glu(OtBu)-OH 1.0 mmol

9) Fmoc-L-Lys(Boc)-OH 1.0 mmol
   Boc: benzyloxycarbonyl

10) Fmoc-L-Gln(Trt)-OH 1.0 mmol
    Trt: trityl

11) Fmoc-L-Ser(tBu)-OH 1.0 mmol
    tBu: t-butyl

12) Fmoc-L-Asp(OBzl)-OH 1.0 mmol
    OBzl: O-benzyl

The protected peptide resin (300 mg) obtained in the above process was admixed with 5 ml of an acetic acid/ trifluoroethanol/dichloromethane (1:1:8) mixture, the mixture was stirred at room temperature for 30 minutes and then filtered to thereby separate the side chain-protected peptide liberated with the weak acid from the resin, and ether was added to the filtrate in the conventional manner. To the thus-obtained precipitate was added an appropriate amount of acetonitrile, followed by lyophilization. By causing the carboxyl group of the C terminal Gly of this side chain-protected dodecapeptide to condense with the amino group of the amino terminal Asp(OBzl) thereof, a cyclic dodecapeptide was synthesized as follows.

The side chain-protected linear dodecapeptide (130 mg) was dissolved in 80 ml of a dimethylformamide solution containing 10% trifluoroethanol, 5 times the amount of the peptide of benzotriazol-1-yloxytris(dimethylamino)phosphonium hexafluorophosphate (abbr.: BOP), the mixture was allowed to stand at room temperature for 24 hours to thereby allow the reaction to proceed, and 80 mg of a side chain-protected cyclic peptide was recovered by the conventional method.

Figure 2:
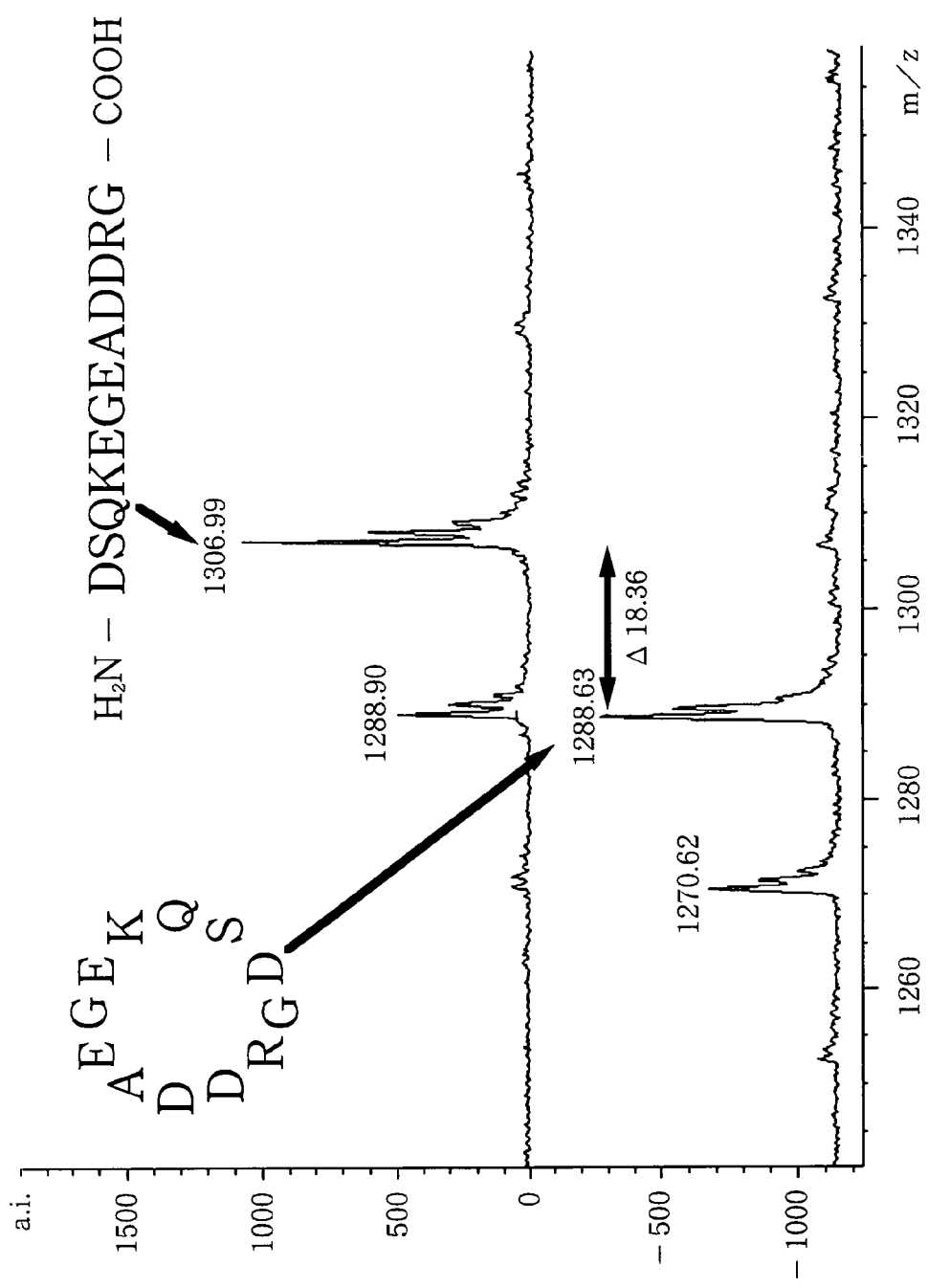

This side chain-protected cyclic dodecapeptide was dissolved in 10 ml of dimethylformamide, 50 mg of palladium-carbon was added, catalytic reduction was carried out using hydrogen gas for 24 hours, and a carboxymethyl side chain-protected cyclic dodecapeptide (15 mg) was obtained by the conventional method. For identifying the cyclic dodecapeptide, all the protective groups were eliminated in the conventional manner and laser mass spectrometry was performed (MALDI-TOF mass spectrometer). The theoretical values and measured values for the cyclic peptide and linear (noncyclic) peptide are given below in Table 1. In FIG. 2, the MALDI TOF mass spectra for the cyclic peptide and linear (noncyclic) peptide are shown. The cyclic dodecapeptide was thus identified based on the results shown (reduction by molecular mass of water 18 as a result of dehydration condensation under ring formation).

TABLE 1

| | Mass | Theoretical value | Measurement value |
|---|---|---|---|
| Cyclic peptide | 1287.53 | 1288.53 | 1288.54 |
| Linear (noncyclic) peptide | 1305.54 | 1306.55 | 1306.73 |

(2) Preparation of Immunogen Comprising Cyclic Dodecapeptide-MAP (Abbr.: CDP-MAP)

The carboxyl group of the carboxymethyl side chain-blocked cyclic dodecapeptide (abbr.: CM-SBCDP) was condensed with the amino group of tetra-branching polylysine of a MAP resin by the BOP method, as follows.

70 mg (32 µmol) of the MAP-resin (0.46 mmol tetra-branching polylysine/resin) was swelled in dimethylformamide (DMF) and the MAP-resin was deprotected (elimination of Fmoc) three times with 10 ml of 20% piperidine/dimethylformamide, washed three times with 5-ml portions of isopropanol and then separated from the isopropanol, to expose the amino terminus of the tetra-branching polylysine. To this MAP-resin was added 10 ml (32 µmol) of a solution of the carboxymethyl side chain-blocked cyclic dodecapeptide in dimethylformamide and the binding between them was effected by the BOP method. The peptide was cleaved from the side chain-blocked cyclic dodecapeptide (abbr.: SBCDP)-MAP-resin in the conventional manner by treatment with trifluoroacetic acid (abbr.: TFA), whereby 12 mg of the cyclic dodecapeptide-MAP (abbr.: CDP-MAP) was obtained. This was used as an immunogen for preparing anti-cyclic dodecapeptide (abbr.: Anti-CDP) monoclonal antibodies.

(3) Preparation of CDP-Pin Resin (Crown Resin) as Assaying Antigen for Preparing Anti-Cyclic Dodecapeptide (Anti-CDP) Monoclonal Antibodies The assaying antigen for efficiently producing anti-CDP monoclonal antibodies from culture supernatants was prepared in the following manner. The side chain-blocked cyclic dodecapeptide was bound to β-Ala at the pointed end of the pin resin (crown resin) according to the epitope scanning kit manual (Chiron Mimotopes Pty Ltd, Clayton, Victoria, Australia) to give a CDP-pin resin (crown resin).

(4) Preparation of Monoclonal Antibody-Producing Hybridomas

Balb/c mice were primarily immunized using the cyclic dodecapeptide-MAP as the immunogen peptide and cell fusion was carried out in the conventional manner using myeloma cells (P3U1) and polyethylene glycol. After fusion, selective culture was carried out using HAT medium and, for the wells in which hybridoma cells formed colonies, the antibody titer in each culture supernatant was determined by the multi-pin ELISA method using the antigen peptide. For each cell group judged as antibody-positive, cloning was performed twice by limiting dilution and a monoclonal antibody-producing hybridoma line was established by the conventional method. For basal immunization, the lyophilized immunogen peptide was dissolved in PBS(-) to a concentration of 1 mg/ml and this solution was admixed, at a ratio of 1:1.2 to 1:1.4, with the immunostimulator Freund's complete adjuvant (FCA) or Freund's incomplete adjuvant (FIA), and the thus-prepared emulsion was used. This emulsion was intraperitoneally administered at a dose of 400 µl/mouse four times in total at one-week intervals. For the first two administrations, an emulsion with FCA was used and, for the last two administrations, an emulsion with FIA was used. The final or boost immunization was carried out after the lapse of one month following completion of the basal immunization by intravenous administration, through the caudal vein, of a 200 µg/ml solution of the lyophilized immunogen peptide (MAP) in PBS(-) at a dose of 200 µl/mouse.

① Preparation of Splenic Cells and Cell Fusion

The preparation of splenic cells and cell fusion were carried out in the conventional manner. Three or four days after the final immunization, mice were sacrificed by exsanguination, splenocytes were excised and loosened in Hank's balanced salt solution (HBSS) and deprived of erythrocytes by hemolytic buffer treatment and centrifugation. The splenic cells thus prepared were mixed with P3U1 cells at a ratio of P3U1:splenic cells=1:8 to 1:10 and the mixture was centrifuged. A polyethylene glycol solution was added to the pellet obtained to thereby effect fusion. After fusion, the fused cells were gently suspended in HAT medium and the suspension was distributed in the wells of 48-well plates and cultured at 37 until the fused cells formed colonies.

② Screening for Antibody-Producing Hybridomas

Screening for specific antibody-producing hybridomas was effected and the desired hybridomas were selected by continuously carrying out primary screening by the ELISA method using the immunogen peptide as a solid phase antigen and secondary screening using the multi-pin peptide as a solid phase antigen. In ELISA, the hybridoma culture supernatant was used as a primary antibody, peroxidase (POD)-labeled anti-mouse IgG as a secondary antibody, TMBZ (3,3 5,5 tetramethylbenzidine) as a color substrate, and 0.3 N $H_2SO_4$ as color development stop solution, and the absorbances were measured at a dominant wavelength of 450 nm and at a reference wavelength of 630 nm.

③ Cloning of a Desired Antibody-Producing Hybridoma Line

A monoclonal hybridoma strain showing high antibody titer in the screening assay was subjected to limiting dilution to one cell/well. The thus-cloned cells were distributed, together with feeder cells prepared from the murine thymus, into the wells of 96 well plates and cultured. After two repetitions of this cloning procedure, the group of monoclonal cells was subjected to screening by multi-pin ELISA using the antigen peptide. The cell line which showed the highest antibody titer in both ELISA screenings was selected as the monoclonal antibody-producing hybridoma line and the monoclonal antibody was purified from the culture supernatant thereof in the conventional manner. The subclass of this monoclonal antibody was found to be IgM κ. This hybridoma was deposited on Feb. 3, 1998 with the Agency of Industrial Science and Technology National Institute of Life Science and Human Technology under accession number FERM P-17198 and this deposit was transferred on Oct. 27, 1998 to an international deposit under the Budapest Treaty under the accession number FERM BP-6925. The cell line established was extended and cultured and the cells were frozen and stored in a liquid nitrogen tank.

(5) Anti-HIV Activity Assay

The anti-HIV activity was measured by the method of Maeda et al. (Y. Maeda, et al., 12th World AIDS Conference Geneva, Abstract P4, Jun. 28-Jul. 3, 1998). The culture fluid of the anti-CDP monoclonal antibody-producing cells created by the present inventors and that of the corresponding non-antibody-producing cells as a control as obtained under the same conditions were used. The antibody-containing culture fluid (200 μl) reduced the rate of infection with HIV-1 virus to 61% in 30 minutes and to 35% in 60 minutes as compared with the control and thus was established that it inhibits the infectivity of HIV-1 virus.

INDUSTRIAL APPLICABILITY

The cyclic peptide of the invention is a novel compound and is useful as an antigen for producing, in vivo, a neutralizing antibody (antibody having an anti-HIV-1 virus activity) capable of neutralizing the HIV-1 virus infection via the second receptor called CXCR4 and/or CCR5. It is also useful as an active agent of an AIDS vaccine.

The invention claimed is:

1. A cyclic peptide represented by the formula:

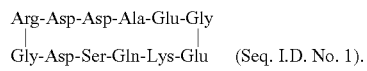
(Seq. I.D. No. 1).

2. A cyclic peptide as claimed in claim 1, wherein a substituent group is bonded to at least one active group selected from among the carboxyl, amino and hydroxyl groups contained in the cyclic peptide.

3. A cyclic peptide as claimed in claim 2 wherein the substituent group is selected from among the residue of a fatty acid $CH_3(CH_2)_n$—COOH (n: 0 to 20), the residue of an alcohol $CH_3(CH_2)_n$—OH (n: 0 to 20) and the unsaturated compound residues corresponding to those compound residues.

* * * * *